US00PP18636P2

(12) United States Plant Patent
Murakami et al.

(10) Patent No.: US PP18,636 P2
(45) Date of Patent: Mar. 18, 2008

(54) ***FUCHSIA* PLANT NAMED 'SANIFPECO'**

(50) Latin Name: *Fuchsia×hybrida*
Varietal Denomination: Sanifpeco

(75) Inventors: Yasuyuki Murakami, Shiga (JP); Mito Ikeda, Hyogo (JP); Hidefumi Funakoshi, Hyogo (JP); Yasuo Kishimoto, Hyogo (JP)

(73) Assignees: Nishinomiya City, Hyogo (JP); Suntory Flowers Limited, Tokyo (JP)

( * ) Notice: Subject to any disclaimer, the term of this patent is extended or adjusted under 35 U.S.C. 154(b) by 0 days.

(21) Appl. No.: 11/520,892

(22) Filed: Sep. 14, 2006

(51) Int. Cl.
*A01H 5/00* (2006.01)

(52) U.S. Cl. ..... Plt./300
(58) Field of Classification Search ..... Plt./300
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Fuchsia* plant named 'Sanifpeco', characterized by its compact and outwardly arching growth habit; freely branching plant habit; bushy habit; lavender and light pink bi-colored flowers; freely and continuous flowering habit; long flowering period; and relatively tolerant to low and high temperatures.

1 Drawing Sheet

Botanical designation: *Fuchsia×hybrida.*
Cultivar denomination: 'Sanifpeco'.

BACKGROUND OF THE INVENTION

The present invention relates to a new and distinct cultivar of *Fuchsia,* botanically known as *Fuchsia×hybrida* and hereinafter referred to by the name 'Sanifpeco'.

The new *Fuchsia* is a product of a planned breeding program conducted by the Inventors in Hyogo, Japan. The objective of the breeding program is to create new outwardly arching *Fuchsia* cultivars with numerous flowers and attractive flower coloration.

The new *Fuchsia* originated from a cross-pollination made by the Inventor in 2000 in Hyogo, Japan of a proprietary selection of *Fuchsia×hybrida* identified as code number aos-6, not patented, as the female, or seed, parent with a proprietary selection of *Fuchsia×hybrida* identified as code number anv-1, not patented, as the male, or pollen, parent. The new *Fuchsia* was discovered and selected by the Inventor as a single flowering plant within the progeny of the stated cross-pollination in a controlled environment in Hyogo, Japan.

Asexual reproduction of the new *Fuchsia* by terminal cuttings in a controlled environment in Hyogo, Japan since January, 2003, has shown that the unique features of this new *Fuchsia* are stable and reproduced true to type in successive generations.

SUMMARY OF THE INVENTION

The cultivar Sanifpeco has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sanifpeco'. These characteristics in combination distinguish 'Sanifpeco' as a new and distinct cultivar of *Fuchsia:*

1. Compact and outwardly arching growth habit.
2. Freely branching plant habit; bushy habit.
3. Lavender and light pink bi-colored flowers.
4. Freely and continuous flowering habit; long flowering period.
5. Relatively tolerant to low and high temperatures.

Plants of the new *Fuchsia* differ primarily from plants of the female parent selection in the following characteristics:

1. Plants of the new *Fuchsia* have smaller leaves than plants of the female parent selection.
2. Plants of the new *Fuchsia* have smaller flowers than plants of the female parent selection.
3. Plants of the new *Fuchsia* and the female parent selection differ in petal and sepal coloration.

Plants of the new *Fuchsia* differ primarily from plants of the male parent selection in the following characteristics:

1. Plants of the new *Fuchsia* have flat leaves whereas plants of the male parent selection have wavy leaves.
2. Plants of the new *Fuchsia* and the male parent selection differ in sepal and pistil coloration.

Plants of the new *Fuchsia* can also be compared to plants of the cultivar Sanicomf, disclosed in U.S. Plant Pat. No. 10,453. In side-by-side comparisons conducted in Hyogo, Japan, plants of the new *Fuchsia* and the cultivar Sanicomf differed in the following characteristics:

1. Plants of the new *Fuchsia* were larger than plants of the cultivar Sanicomf.
2. Plants of the new *Fuchsia* had thinner lateral branches than plants of the cultivar Sanicomf.
3. Plants of the new *Fuchsia* had broader leaves and shorter petioles than plants of the cultivar Sanicomf.
4. Plants of the new *Fuchsia* and the cultivar Sanicomf differed in petal, sepal, style and stigma color.
5. Plants of the new *Fuchsia* had longer and narrower sepals than plants of the cultivar Sanicomf.
6. Plants of the new *Fuchsia* had longer and thicker peduncles than plants of the cultivar Sanicomf.

BRIEF DESCRIPTION OF THE PHOTOGRAPHS

The accompanying colored photographs illustrate the overall appearance of the new *Fuchsia,* showing the colors as true as it is reasonably possible to obtain in colored reproductions of this type. Colors in the photographs may differ slightly from the color values cited in the detailed botanical description which accurately describe the colors of the new *Fuchsia.*

The photograph at the top of the sheet comprises a side perspective view of the typical flowering plant of 'Sanifpeco' grown in a container.

The photograph at the bottom of the sheet comprises a close-up of typical flowers and leaves of 'Sanifpeco'.

DETAILED BOTANICAL DESCRIPTION

The photographs and following observations, measurements and values describe plants grown in Hyogo, Japan, under commercial practice in a polyethylene-covered greenhouse with day temperatures ranging from 15° C. to 32° C. and night temperatures ranging from 10° C. to 25° C. Plants were grown for about one year with one plant per 13.5-cm container. In the following description, color references are made to The Royal Horticultural Society Colour Chart, 2001 Edition, except where general terms of ordinary dictionary significance are used.

Botanical classification: *Fuchsia×hybrida* cultivar Sanifpeco.

Parentage:

*Female, or seed, parent.*—Proprietary selection of *Fuchsia×hybrida* identified as code number aos-6, not patented.

*Male, or pollen, parent.*—Proprietary selection of *Fuchsia×hybrida* identified as code number anv-1, not patented.

Propagation:

*Type.*—By terminal cuttings.

*Time to initiate roots.*—About one week at temperatures of 20° C.

*Time to produce a rooted young plant.*—About three weeks at temperatures of 20° C.

*Root description.*—Fine, fibrous; yellowish white in color.

*Rooting habit.*—Freely branching.

Plant description:

*Plant and growth habit.*—Initially upright, then outwardly spreading; compact. Freely branching; with lateral branches developing potentially at every node; bushy habit. Vigorous growth habit.

*Plant height.*—About 35 cm.

*Plant diameter.*—About 40 cm.

Lateral branch description:

*Length.*—About 20 cm.

*Diameter.*—About 1.5 mm.

*Internode length.*—About 2.3 cm.

*Strength.*—Strong.

*Aspect.*—Initially upright to outwardly arching.

*Texture.*—Pubescent.

*Color.*—147D tinted with close to 187A.

Foliage description:

*Arrangement.*—Opposite, simple.

*Length.*—About 4.2 cm.

*Width.*—About 2.2 cm.

*Shape.*—Ovate.

*Apex.*—Acute.

*Base.*—Obtuse with cordate tendencies.

*Margin.*—Mostly entire with shallow serrations and ciliation.

*Texture, upper surface.*—Smooth, glabrous.

*Texture, lower surface.*—Smooth, glabrous.

*Venation pattern.*—Pinnate; reticulate.

*Color.*—Developing foliage, upper surface: 137B. Developing foliage, lower surface: 138A. Fully expanded foliage, upper surface: 137A; venation, similar to lamina. Fully expanded foliage, lower surface: 138A; venation, similar to lamina.

*Petiole.*—Length: About 6 mm. Diameter: About 1.2 mm. Texture, upper and lower surfaces: Smooth, glabrous. Color, upper and lower surfaces: 144D.

Flower description:

*Flower arrangement and habit.*—Single bi-colored axillary flowers. Flowers initially upright and then pendulous. Flowers not fragrant. Freely flowering habit with potentially two flowers per leaf axil. Flowers not fragrant.

*Natural flowering season.*—Long flowering period; in Japan, plants flower from spring to fall; flowering continuous during this period. Flowers last about three to four days on the plant. Flowers not persistent.

*Flower diameter.*—About 4.2 cm.

*Flower height (depth).*—About 3.1.

*Flower buds.*—Shape: Lenticular. Length: About 3.9 cm. Diameter: About 9.5 mm. Color: 73D.

*Petals.*—Arrangement: Four in a single whorl. Length: About 2.1 cm. Width: About 1.6 cm. Shape: Obovate. Apex: Rounded. Base: Truncate. Margin: Entire. Texture, upper and lower surfaces: Smooth, glabrous; satiny. Color: When opening, upper and lowers surfaces: N88C. Fully opened, upper and lower surfaces: N78C.

*Sepals.*—Arrangement: Calyx star-shaped with four sepals fused at the base. Calyx tube length: About 9.2 mm. Calyx tube diameter: About 3.8 mm. Sepal lobe length: About 3.2 cm. Sepal lobe width: About 7 mm. Shape: Lanceolate. Apex: Acute. Margin: Entire. Texture, upper and lower surfaces: Smooth, glabrous. Color: When opening and fully opened, upper surface: 69B. When opening and fully opened, lower surface: 69C.

*Peduncles.*—Length: About 2.9 cm. Diameter: About 1 mm. Angle: Arching. Strength: Moderately strong. Texture: Sparsely pubescent. Color: N144C.

*Reproductive organs.*—Stamens: Quantity: Eight per flower. Anther shape: Ellipsoidal. Anther size: About 3.8 mm by 1.4 mm. Anther color: Close to 186C. Pollen amount: Moderate. Pollen color: 2D. Pistils: Quantity: One per flower. Pistil length: About 4.5 cm. Style color: 69C to 69D. Stigma shape: Ellipsoidal. Stigma color: 4D. Ovary color: 143C.

*Seed/fruit.*—Seed and fruit development have not been observed on plants of the new *Fuchsia.*

Temperature tolerance: Plants of the new *Fuchsia* have good temperature tolerance and have been observed to tolerate temperatures from about −2° C. to about 33° C.

Pathogen/pest resistance: Plants of the new *Fuchsia* have not been observed to be resistant to pests and pathogens common to *Fuchsia.*

It is claimed:

1. A new and distinct *Fuchsia* plant named 'Sanifpeco' as illustrated and described.

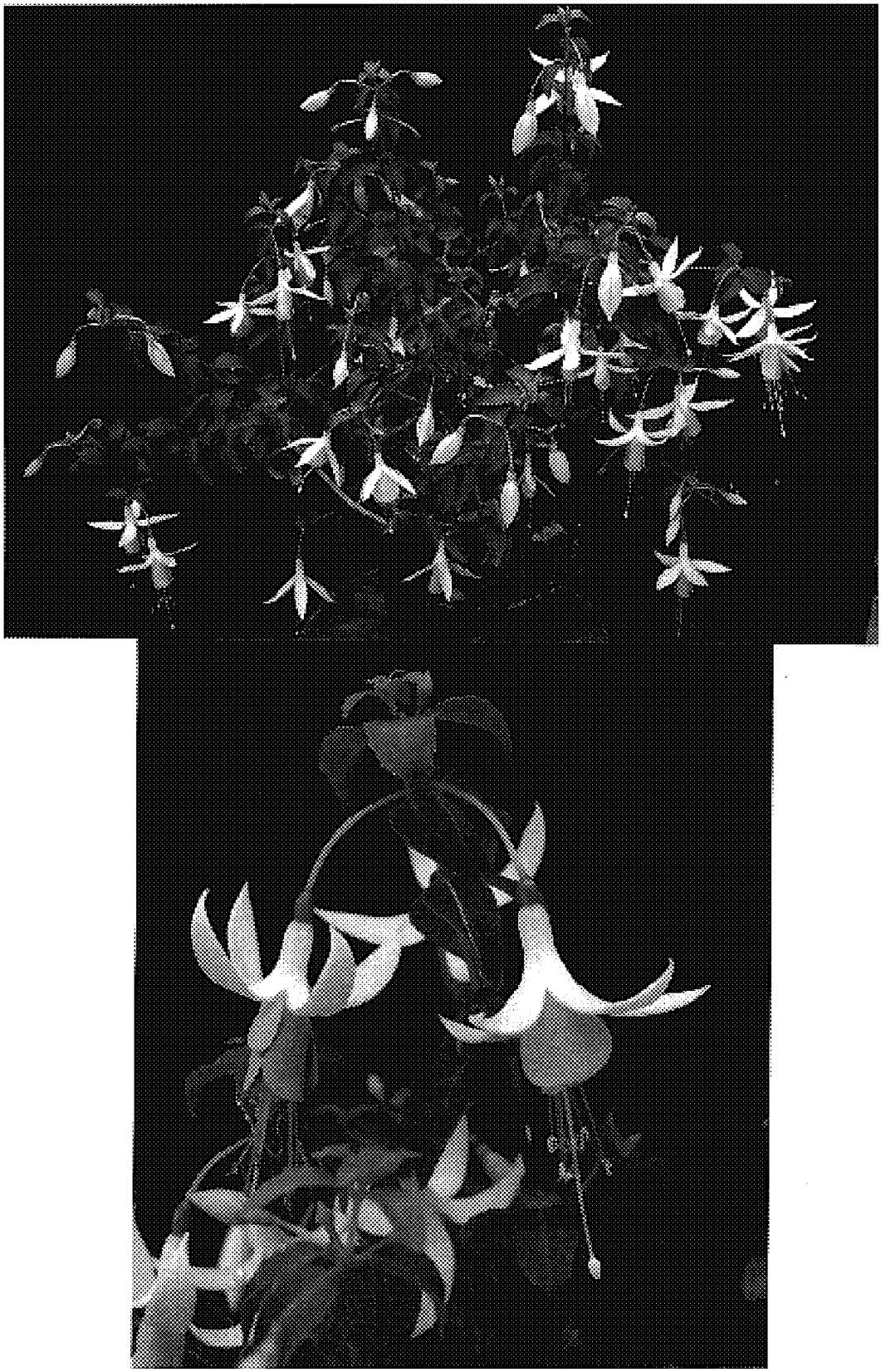

* * * * *